United States Patent
Thornton et al.

(10) Patent No.: US 9,468,746 B2
(45) Date of Patent: Oct. 18, 2016

(54) SYSTEMS AND METHODS FOR LOCAL BIOACTIVE MATERIAL DELIVERY

(75) Inventors: Ronan Thornton, Co. Galway (IE); Sean Whelan, Co. Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 2399 days.

(21) Appl. No.: 11/466,322

(22) Filed: Aug. 22, 2006

(65) Prior Publication Data
US 2008/0097570 A1 Apr. 24, 2008

(51) Int. Cl.
| A61F 2/06 | (2013.01) |
| A61M 29/02 | (2006.01) |
| A61F 2/07 | (2013.01) |
| A61B 17/00 | (2006.01) |
| A61M 25/04 | (2006.01) |
| A61M 25/10 | (2013.01) |
| A61F 2/89 | (2013.01) |

(52) U.S. Cl.
CPC ............. *A61M 29/02* (2013.01); *A61F 2/07* (2013.01); *A61B 2017/00243* (2013.01); *A61B 2017/00889* (2013.01); *A61B 2017/00893* (2013.01); *A61F 2/89* (2013.01); *A61F 2250/0067* (2013.01); *A61M 25/04* (2013.01); *A61M 2025/105* (2013.01); *A61M 2025/1054* (2013.01)

(58) Field of Classification Search
CPC ............. A61F 2/04; A61F 2/06; A61F 2/07; A61F 2/91; A61M 29/02
USPC ............. 623/1.27, 1.15, 1.13, 23.65, 23.66
See application file for complete search history.

(56) References Cited

U.S. PATENT DOCUMENTS

| 5,049,132 | A | | 9/1991 | Shaffer et al. | |
|---|---|---|---|---|---|
| 5,102,402 | A | | 4/1992 | Dror et al. | |
| 5,181,911 | A | | 1/1993 | Shturman | |
| 5,181,971 | A | | 1/1993 | Ohtsuka | |
| 5,199,951 | A | | 4/1993 | Spears | |
| 5,704,352 | A | | 1/1998 | Tremblay et al. | |
| 5,716,340 | A | | 2/1998 | Schweich et al. | |
| 5,833,658 | A | | 11/1998 | Levy et al. | |
| 6,052,613 | A | | 4/2000 | Takaki | |
| 6,312,457 | B1 | * | 11/2001 | DiMatteo et al. | 623/1.13 |
| 6,632,196 | B1 | | 10/2003 | Houser | |
| 7,288,111 | B1 | * | 10/2007 | Holloway et al. | 623/1.15 |
| 7,435,255 | B1 | * | 10/2008 | Rao | 623/1.42 |
| 7,481,835 | B1 | * | 1/2009 | Pacetti et al. | 623/1.15 |
| 2002/0072511 | A1 | * | 6/2002 | New et al. | 514/182 |

(Continued)

FOREIGN PATENT DOCUMENTS

| EP | 0808613 | 11/1997 |
|---|---|---|
| WO | WO97/03717 | 2/1997 |

(Continued)

OTHER PUBLICATIONS

Wilensky et al., "Methods and Devices for Local Drug Delivery in Coronary and Peripheral Arteries," Trend Cardiovasc Med, vol. 3 (1993).

(Continued)

*Primary Examiner* — Jason-Dennis Stewart (57) ABSTRACT

Disclosed herein are removable devices adapted to allow localized and contained delivery of bioactive materials to a treatment site within a lumen such as a blood vessel such that the flow of fluid through the lumen is not blocked during bioactive material delivery.

7 Claims, 4 Drawing Sheets

(56) References Cited

U.S. PATENT DOCUMENTS

2002/0169497 A1* 11/2002 Wholey et al. .............. 623/1.13
2004/0193283 A1* 9/2004 Rioux et al. ............... 623/23.66

FOREIGN PATENT DOCUMENTS

| WO | WO97/41915 | 11/1997 |
| WO | WO00/48645 | 8/2000 |
| WO | WO02/076345 | 10/2002 |
| WO | WO03/096932 | 11/2003 |
| WO | WO2005/030093 | 4/2005 |
| WO | WO2006/104649 | 10/2006 |

OTHER PUBLICATIONS

Takaki, "Fiber-Optic Transducer Aids Heart Monitoring" Engineering News, Jun. 7, 1999.

* cited by examiner

SYSTEMS AND METHODS FOR LOCAL BIOACTIVE MATERIAL DELIVERY

FIELD OF THE INVENTION

The present invention relates to systems and methods that allow a bioactive material to be locally delivered to a treatment site within a lumen while not impeding the flow of fluid or other material through the lumen.

BACKGROUND OF THE INVENTION

Disease, injury, surgery or other disorders can lead to localized tissue damage. When bioactive materials are administered orally or parenterally to treat a local disorder, they often must be given in large amounts so that an effective amount of the bioactive material reaches the treatment site. These large amounts of administered bioactive materials can produce harmful side effects in other areas of the body where treatment is not needed. Thus, one significant challenge in the medical and pharmaceutical industry has been to deliver an effective amount of a bioactive material locally at a treatment site without producing unwanted systemic side effects.

A prime example of a situation where local therapy is needed with bioactive materials that produce unwanted systemic side effects is in the prevention of complications following the placement of a cardiovascular prosthetic device such as a prosthetic vascular graft, patch, or stent used to repair a damaged vessel. With the implantation of stents in particular (tubular devices intended to hold vessels or other lumens open and clear), restenosis, a re-narrowing of the vessel can occur. To prevent this re-narrowing, numerous pharmacological agents have been tested. Unfortunately, none have yet demonstrated an unequivocal reduction in the incidence of restenosis. One reason for the failure of these pharmacological therapies may be due to ineffective administration routes or protocols adopted to avoid the serious side-effects that could result from systemic administration of the proper dosage.

To address this problem, various researchers have proposed devices and methods for site-specific delivery of bioactive materials. Some of the proposed methods have included the systemic administration of therapeutic agents that have a specific affinity for the injured or diseased tissue or systemic administration of inactive agents followed by local activation. When dealing with the treatment of a vessel in particular, proposed methods have included the direct deposition of bioactive materials into an arterial wall through an intravascular delivery system and the local placement of bioactive material coated stents. Wilensky et al., Methods and Devices for Local Drug Delivery in Coronary and Peripheral Arteries, Trend Cardiovasc Med, vol. 3 (1993).

Other attempts to locally deliver bioactive materials to lumens have included angioplasty catheter dilation balloons with coatings of bioactive materials on the external surface of the balloon (e.g., U.S. Pat. Nos. 5,102,402 and 5,199,951). Other balloon catheters contain perforations in the wall of the balloon for infusion of bioactive materials such as the Wolinsky catheter or the "balloon within a balloon design" seen in U.S. Pat. No. 5,049,132. There are also systems that include proximal and distal balloons that are simultaneously inflated to isolate a treatment space within an arterial lumen. In this example, a catheter extends between the two balloons and includes a port that can deliver bioactive materials to the space between the inflated balloons. These approaches, however, often disrupt fluid flow through the lumen and reduce distal tissue perfusion during bioactive material delivery. Other catheters such as the Stack perfusion catheter and the catheter embodied in U.S. Pat. No. 5,181,911 were designed to facilitate drug delivery without disrupting distal tissue perfusion. These devices, however, are bulky and limited in their clinical applications.

The efficacy of the described devices and methods turns on a number of factors including the local conditions and vasculature of the treatment site. For instance, one efficacy factor includes the amount of time that a delivered bioactive material will stay resident locally before being carried downstream by circulating fluids, including in one example, circulating blood. To the extent these systems allow the bioactive materials to be carried away from the treatment site, they run the risk of applying the bioactive material to areas of the body where such agents may not be beneficial and leaving the intended area untreated. Further, and as stated, a number of the described devices and methods block the flow of fluids through the lumen during bioactive material delivery. This blockage can reduce the effectiveness of the described devices and methods by leading to unwanted side effects related to the blockage of fluid flow through the lumen.

Based on these issues, there exists a need in the art for systems and methods that can deliver and sustain appropriate concentrations of bioactive materials at a treatment site within a lumen without blocking fluid flow through the lumen during bioactive material delivery. The present invention provides such systems and methods.

SUMMARY OF THE INVENTION

The present invention provides systems and methods that can deliver and sustain appropriate concentrations of bioactive materials at a treatment site within a lumen without blocking fluid flow through the lumen. The present invention provides this benefit by providing a tubular structure comprised of two or more ring members connected by a biocompatible covering. The ring members can expand to a diameter that is larger than the natural diameter of the biocompatible covering. When positioned at a treatment site within a lumen, the ring members expand to a diameter that is larger than the natural diameter of the biocompatible covering. The expansion of the ring members creates a seal between the ring members and a lumen wall. Due to its smaller natural diameter, the biocompatible covering that is not in direct contact with a ring member will trend slightly inwards towards the center of the lumen. This inwards trend of the biocompatible covering creates a space between its outer surface and the lumen wall between the ring members. This space provides an area where bioactive materials can be delivered and not exposed to the currents of fluid flow through the lumen so that they remain at the intended treatment site. In addition, fluid can continue to flow through the interior of the tubular structure during bioactive material delivery into the described spaces.

Specifically, one embodiment according to the present invention comprises a bioactive material delivery device comprising a tubular structure comprising two or more expandable ring members and a biocompatible covering that connects the ring members into the tubular structure wherein when the ring members are expanded, the ring members expand the diameter of portions of the biocompatible covering not in direct contact with the ring members to a diameter that is less than the diameter of the expanded ring members so that when the bioactive material delivery device is positioned at a treatment site within a lumen, at least one space for bioactive material delivery is created between the outer surface of the biocompatible covering, the inner wall of the lumen and between the ring members.

Ring members of the present invention can be found at both ends of the tubular structure; at the ends of the tubular structure and spaced at regular intervals along the length of the tubular structure; and at the ends of the tubular structure and spaced at irregular intervals along the length of the tubular structure. Ring members can also be undulating ring members at both ends of the tubular structure wherein these undulating ring members are connected by an undulating helical wire along the length of the tubular device. Further, devices according to the present invention can also comprise additional longitudinal or helical structural elements that expand when the expandable ring members expand, such that these additional longitudinal or helical structural elements further define longitudinal or helical channels for bioactive material delivery.

Ring members used in accordance with the present invention can be expanded by a method such as self expansion; self expansion following retraction of a retaining sheath; self expansion following release from a tensioning mechanism; balloon expansion; and combinations thereof.

In one embodiment according to the present invention, the biocompatible covering of the tubular structure comprises one or more injection tubes and associated injection ports wherein the injection ports are located between the ring members. In another embodiment the biocompatible covering is coated with a bioactive material that can be released into the spaces.

The present invention also comprises treatment kits. In one treatment kit according to the present invention, the treatment kit comprises instructional information, a bioactive material delivery device according to the present invention as described above, and an injection catheter. Treatment kits according to the present invention can also further comprise one or more bioactive materials. The instructional information can direct how the bioactive material delivery device and the injection catheter should be used to locally deliver a bioactive material to a lumen treatment site without blocking fluid flow through the lumen.

The present invention also includes methods. One method according to the present invention includes locally treating a lumen wall by positioning a bioactive material delivery device according to the present invention at a portion of a lumen wall needing treatment and delivering a bioactive material.

DEFINITION OF TERMS

Prior to setting forth embodiments according to the present invention, it may be helpful to an understanding thereof to set forth definitions of certain terms that will be used hereinafter. Some terms that are used herein are further described as follows:

The term "bioactive material(s)" refers to any organic, inorganic, or living agent that is biologically active or relevant. For example, a bioactive material can be a protein, a polypeptide, a polysaccharide (e.g. heparin), an oligosaccharide, a mono- or disaccharide, an organic compound, an organometallic compound, or an inorganic compound. It can include a living or senescent cell, bacterium, virus, or part thereof. It can include a biologically active molecule such as a hormone, a growth factor, a growth factor producing virus, a growth factor inhibitor, a growth factor receptor, an anti-inflammatory agent, an antimetabolite, an integrin blocker, or a complete or partial functional insense or antisense gene. It can also include a man-made particle or material, which carries a biologically relevant or active material. An example is a nanoparticle comprising a core with a drug and a coating on the core.

Bioactive materials also can include drugs such as chemical or biological compounds that can have a therapeutic effect on a biological organism. Bioactive materials include those that are especially useful for long-term therapy such as hormonal treatment. Examples include drugs for contraception and hormone replacement therapy, and for the treatment of diseases such as osteoporosis, cancer, epilepsy, Parkinson's disease and pain. Suitable biological materials can include, e.g., anti-inflammatory agents, anti-infective agents (e.g., antibiotics and antiviral agents), analgesics and analgesic combinations, antiasthmatic agents, anticonvulsants, antidepressants, antidiabetic agents, antineoplastics, anticancer agents, antipsychotics, and agents used for cardiovascular diseases such as anti-restenosis and anti-coagulant compounds. Exemplary drugs include, but are not limited to, Zotarolimus (ABT-578), rapamycin, paclitaxel, dexamethasone, everolimus, tacrolimus, des-aspartate angiotensin I, exochelins, nitric oxide, apocynin, gamma-tocopheryl, pleiotrophin, estradiol, heparin, aspirin, atorvastatin, cerivastatin, fluvastatin, lovastatin, pravastatin, rosuvastatin, simvastatin, abciximab, angiopeptin, colchicines, eptifibatide, hirudin, methotrexate, streptokinase, taxol, ticlopidine, tissue plasminogen activator, trapidil, urokinase, vascular endothelial growth factor, transforming growth factor beta, insulin growth factor, platelet-derived growth factor, fibroblast growth factor, and combinations thereof.

Bioactive materials also can include precursor materials that exhibit the relevant biological activity after being metabolized, broken-down (e.g. cleaving molecular components), or otherwise processed and modified within the body. These can include such precursor materials that might otherwise be considered relatively biologically inert or otherwise not effective for a particular result related to the medical condition to be treated prior to such modification.

Combinations, blends, or other preparations of any of the foregoing examples can be made and still be considered bioactive materials within the intended meaning herein. Aspects of the present invention directed toward bioactive materials can include any or all of the foregoing examples.

The term "lumen" includes any area of an organism's body which transports substances and includes, but is not limited to blood vessels of the cardiovascular system (arteries and veins), vessels of the lymphatic system, the intestinal tract (esophagus, stomach, the small and large intestines, and colon), the portal-caval system of the liver, the gall bladder and bile duct, the urinary system (ureters, bladder and urethra), the respiratory system (trachea, bronchi, and bronchioles), and ducts and ductules connecting endocrine organs to other areas of the body.

The phrase "treatment site" includes any portion of a lumen that is intended to receive a beneficial or therapeutic effect of a bioactive material administered with the systems and methods described herein. For example, the treatment site can be, without limitation, a stenotic lesion in a blood vessel, a developing thrombus, a localized tumor or the like.

The term "instructional information" means a description of a product or method and/or how to use the product or method that can allow a physician, pharmacist, and/or patient to make a more informed decision regarding use of the product or method. The instructional information generally will accompany the product it describes, however, instructional information can come in many different forms including, without limitation, a paper insert, a c.d. rom and/or a direction to another source of information describing the product such as a book, brochure, video or website.

DETAILED DESCRIPTION

There exists a need in the art for systems and methods that can deliver and sustain appropriate concentrations of bioactive materials at a treatment site within a lumen without blocking fluid flow through the lumen during bioactive material delivery. The present invention provides such systems and methods. These systems and methods provide removable, expandable, non-occlusive endovascular support devices that can provide prolonged localized delivery of bioactive materials to a lumen treatment site. The systems and methods can also adopt long-term or permanent placement devices. In one non-limiting example of the described systems and methods, the lumen is a blood vessel and the fluid is blood.

Figure 1:
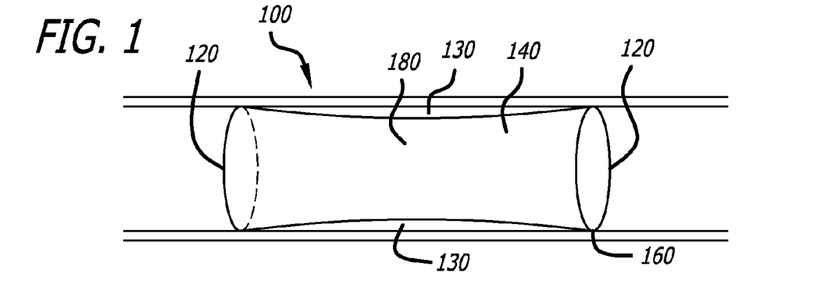
FIG. 1 depicts one embodiment of a tubular structure and ring members according to the present invention.

Referring to FIG. 1, one embodiment according to the present invention comprises a tubular structure 100 comprising at least two ring members 120 covered by a biocompatible covering 140 such as Dacron® (E.I. du Pont de Nemours & Company, Wilmington, Del.) or a fabric-like material woven from a variety of biocompatible polymer fibers. When deployed at a treatment site from a retractable retaining sheath (or through other release means), the ring members 120 expand to ensure a seal against the lumen wall 160. In its free state the biocompatible covering 140 is smaller in diameter than the ring members 120 but is pulled open by the expanded ring members 120. Where the biocompatible covering 140 does not contact a ring member 120, due to its smaller diameter, it will trend inward towards the center of the lumen 180 leaving space 130 between the lumen wall 160 and the outer surface of the biocompatible covering 140. This space 130 provides an area to deliver bioactive materials that will not be washed away from the treatment site by fluid flow through the lumen. Further, fluid flow will not be obstructed through the lumen during bioactive material delivery as fluid can flow through the interior of the tubular structure 100.

Figure 2A:
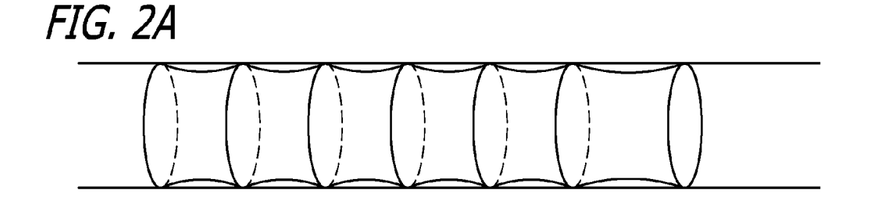
FIGS. 2A-2D depict various alternative embodiments of tubular structures and ring members according to the present invention.
Figure 2B:
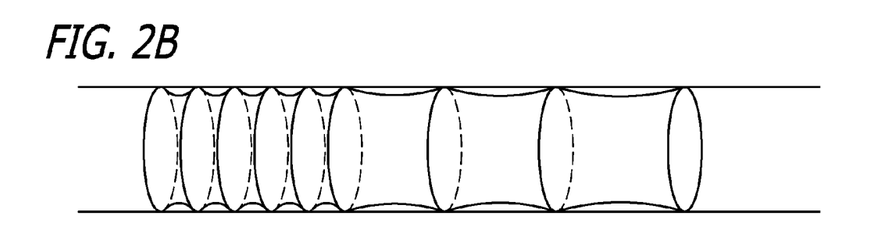
Figure 2C:
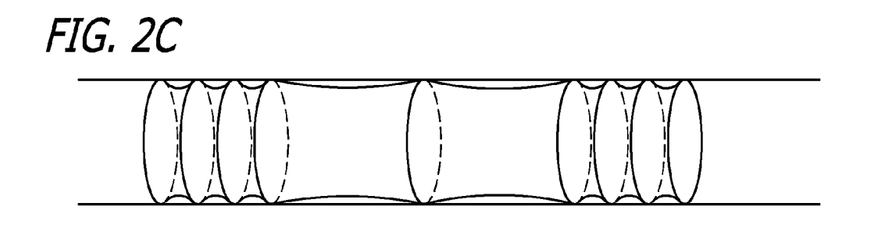
Figure 2D:
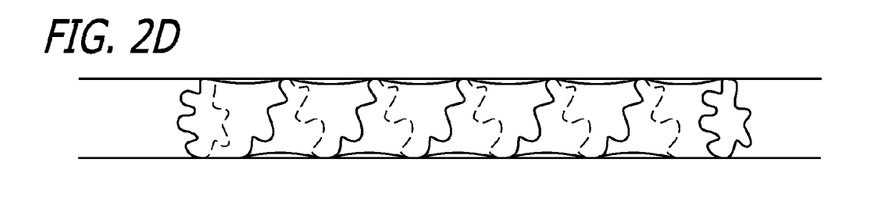

As shown in FIGS. 2A-2D, ring members found on the tubular structures of the present invention can be found at any point along the length of the tubular structure. For instance, in addition to being found at both ends of a tubular structure, ring members can also be found at regular (FIG. 2A) or irregular (FIG. 2B) intervals along the length of the tubular structure. Additional ring members providing more compartmentalized spaces between ring members can allow for even more control over the local delivery of bioactive materials. FIG. 2C depicts one embodiment that allows for bioactive material delivery to be concentrated near the ends of the tubular structure. This embodiment can be beneficial because in some instances transition areas between stented and unstented (or grafted and ungrafted) portions of lumens can benefit from additional therapeutic treatment. As shown in FIG. 2D, the ring members can also be undulating or adopt other appropriate irregular shapes rather than comprising straight rings. In this (and other embodiments such as that depicted in FIG. 1) a single injection tube can be used to bath the whole treatment site with bioactive materials because the space created for bioactive material delivery is continuous.

As stated, spaces for bioactive materials are located between adjacent ring members between the outer surface of the biocompatible covering that does not contact a ring member and the inner surface of a lumen wall at a treatment site. In certain embodiments, longitudinal or helical channels can also be formed between ring members (between either two end ring members or non-end ring members) by including additional structural elements that expand when the ring members expand. These additional structural elements can be attached to the ring members or can be positioned around the outer circumference of the ring members such that they are pushed out when the ring members expand. These additional structural elements can serve to define channels between ring members to further define bioactive material delivery spaces.

In one embodiment according to the present invention the ring members can be self-expanding once deployed from a retractable retaining sheath. In another embodiment ring members can be unsheathed and self-expanding following release from a releasable and replaceable tensioning mechanism. The rings could also be expanded through the inflation of a catheter balloon or other appropriate methods known to those of ordinary skill in the art.

Figure 3:
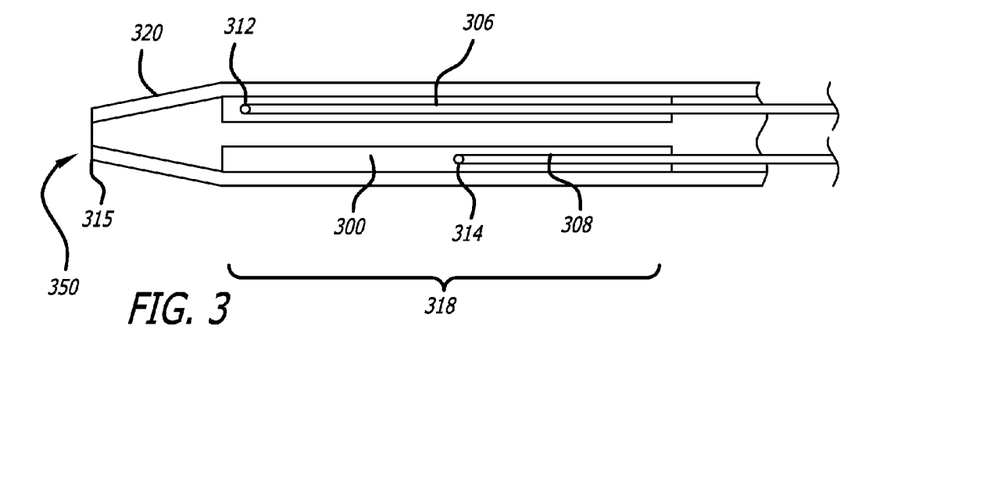
FIG. 3 shows a tubular structure compressed in a catheter for delivery to a treatment site.

In some embodiments, the described tubular structures are provided "pre-loaded" into a delivery and deployment catheter such as that depicted in FIG. 3. The tubular structure 300 is radially compressed to fill the tubular structure chamber 318 in the distal end 315 of catheter 350. The tubular structure 300 is covered with a retractable retaining sheath 320. Within the walls of the biocompatible covering of the tubular structure 300 are one or more injection tubes 306, 308 and injection ports 312, 314 on the surface of the biocompatible covering.

Figure 4:
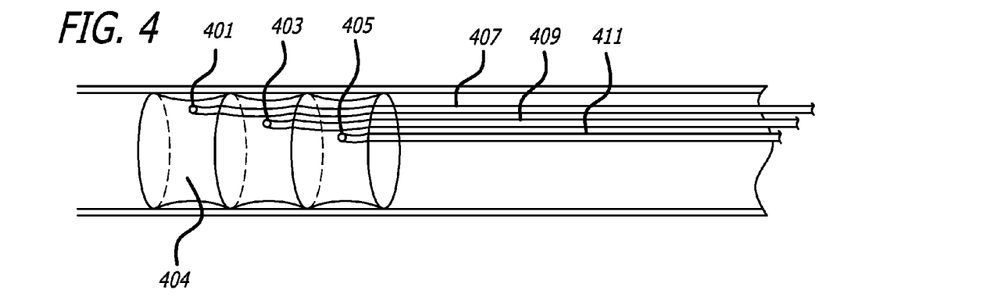
FIG. 4 depicts a tubular structure and bioactive material injection tubes deployed at a treatment site (delivery catheter not shown).

Bioactive material delivery to the described spaces can occur through several different mechanisms. In one embodiment according to the present invention the biocompatible covering can be coated with a bioactive material that will be released over time. Instead of being washed downstream of the treatment site by circulating fluids, the released bioactive materials will remain trapped in the described spaces at the treatment site. Another delivery method can occur as depicted in FIG. 4. FIG. 4 depicts an embodiment of the tubular structure with injection tubes as described in FIG. 3 deployed at a treatment site (delivery catheter not shown). In this depicted embodiment the biocompatible covering 404 can include the distal ends (injection ports) 401, 403, 405 of injection tubes 407, 409, 411 wherein the injection ports 401, 403, 405 are spaced to terminate between the ring members of a tubular structure. The injection tubes 407, 409, 411 travel proximally to outside of a patient's body where bioactive material delivery through them can be appropriately controlled. Each injection port 401, 403, 405 can be connected to the same injection tube or each port can include its own independently controlled injection tube (as depicted) so that more than one bioactive material can be administered to the treatment site simultaneously.

Figure 5A:
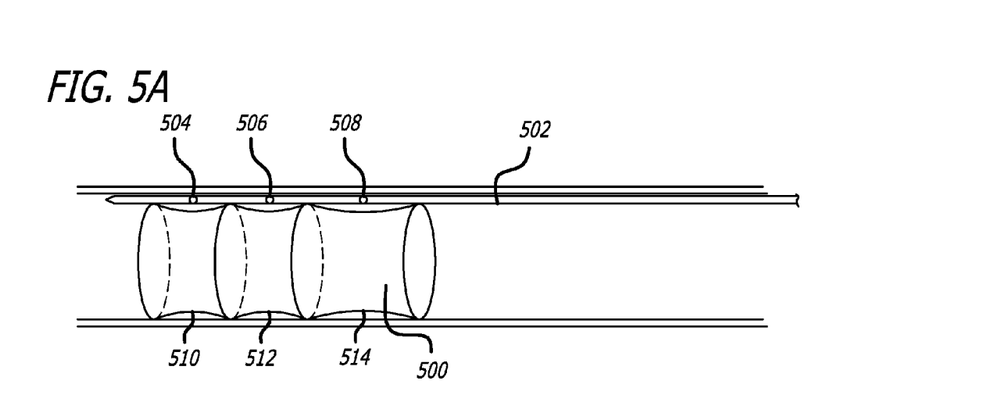
FIGS. 5A-5B depict alternative bioactive material delivery methods in accordance with the present invention.
Figure 5B:
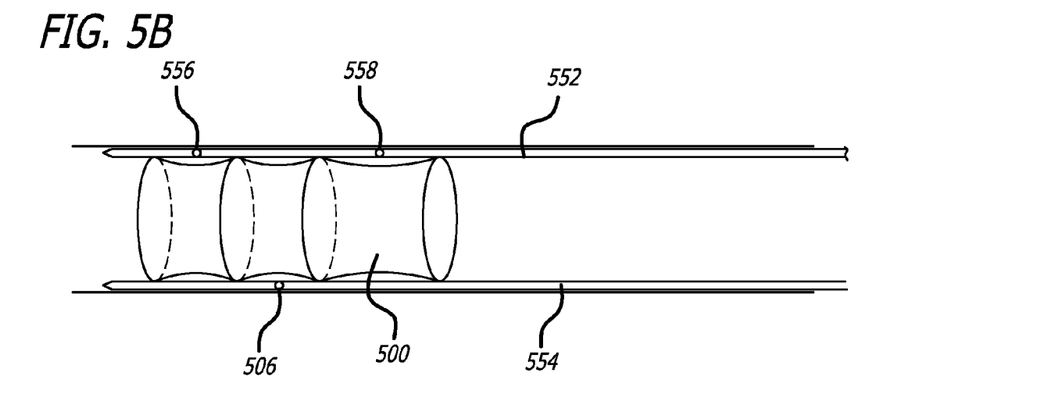

Alternative embodiments according to the present invention can also utilize one or more independently deployed injection catheters. For instance, FIG. 5A depicts an embodiment where one injection catheter 502 with multiple injection ports 504, 506, 508 is deployed to a treatment site. Following the injection catheter's 502 delivery to the treatment site, a tubular structure 500 is positioned at the treatment site so that the spaces 510, 512, 514 that are formed after expansion of the ring members are appropriately positioned with the injection ports 504, 506 508 of injection catheter 502. Alternatively, and as shown in FIG. 5B, more than one injection catheter can be used for bioactive material delivery at a treatment site. In this embodiment, injection catheters 552 and 554 are delivered to the treatment site followed by delivery and deployment of a tubular structure 500 of the present invention. The tubular structure 500 is again appropriately positioned in accordance with the position of injection ports 556, 558, 560. This positioning can be accomplished through a variety of appropriate procedures known to those of ordinary skill in the art. Once positioning has occurred, localized bioactive material delivery can occur in the described spaces where these materials will not be washed away from the treatment site by fluid flow through the lumen.

Figure 6A:
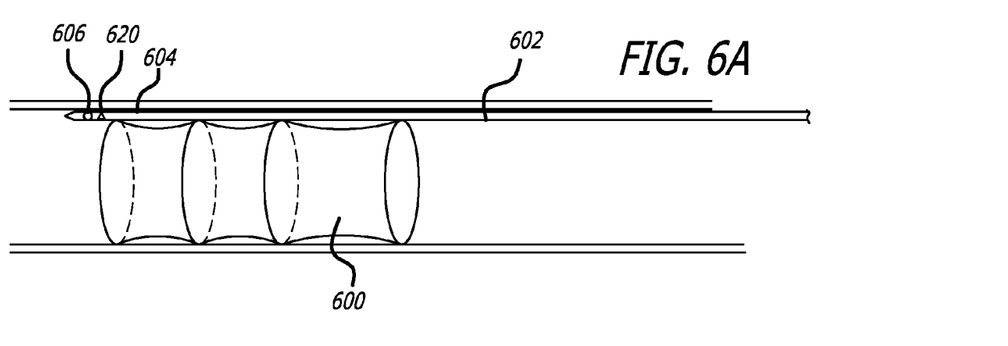
FIGS. 6A-6E depict an additional alternative bioactive material delivery method in accordance with the present invention.
Figure 6B:
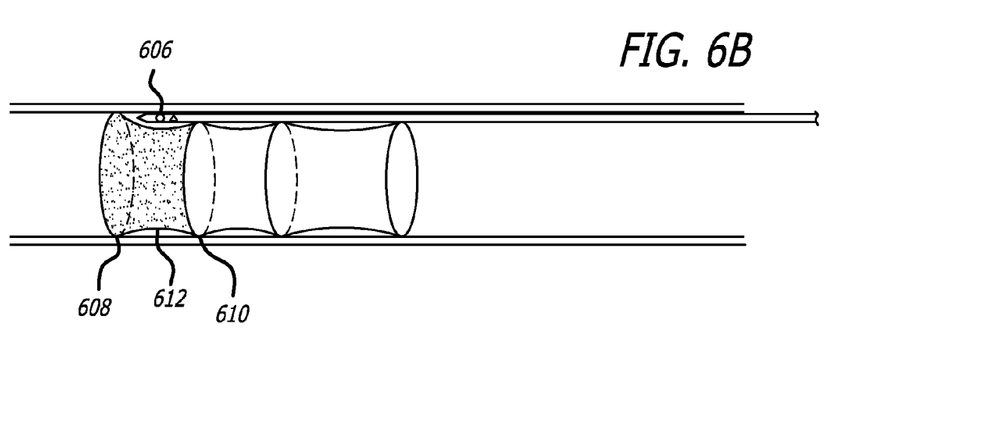
Figure 6C:
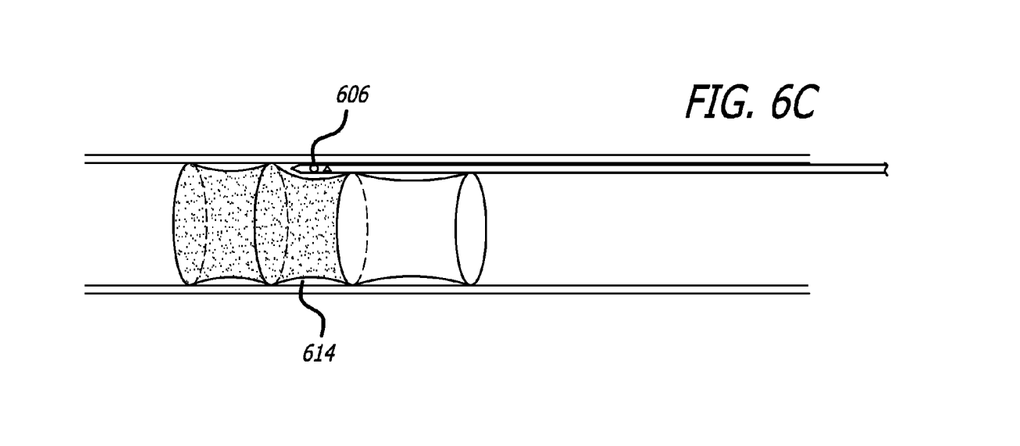
Figure 6D:
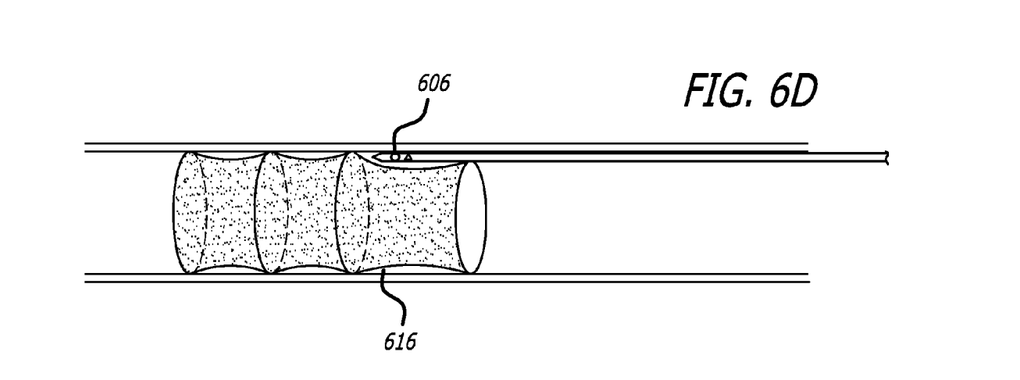
Figure 6E:
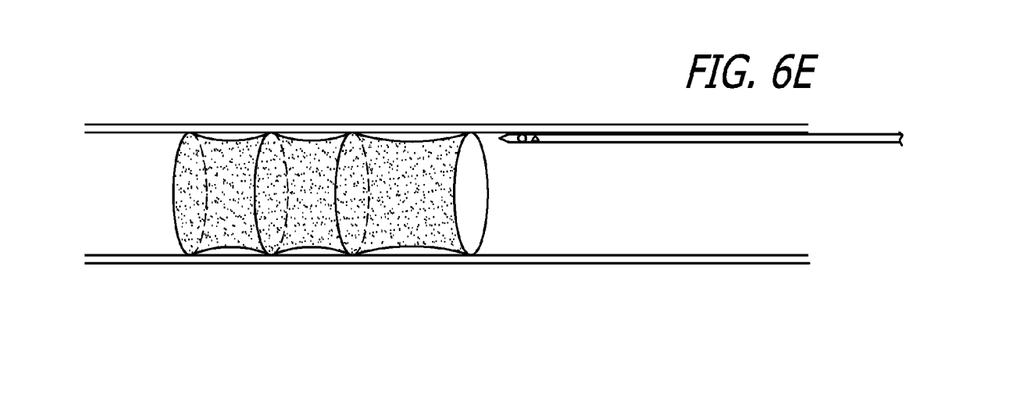

An alternative bioactive material delivery method can encompass that depicted in FIGS. 6A-6E. In this depicted embodiment, an injection catheter 602 is deployed to the area of a treatment site. The distal end and portion of the injection catheter 604 (including injection port 606) are positioned distal to the position where the tubular structure will be deployed. Next, the tubular structure 600 is deployed at the treatment site (FIG. 6A). Once the tubular structure 600 is in place at the treatment site, the injection catheter 602 can be retracted in segments. As shown in FIG. 6B, the injection catheter 602 can first be retracted so that injection port 606 is positioned between the two most distal ring members 608, 610 of the tubular structure 600. While in this position, the injection catheter 602 can deliver bioactive materials to space 612. Following bioactive material delivery to space 612, injection catheter 602 can be retracted further so that injection port 606 is positioned in space 614 (FIG. 6C). Following bioactive material delivery in space 614, injection port 606 can be further retracted to deliver bioactive materials in space 616 as shown in FIG. 6D. Once bioactive materials have been delivered in all desired spaces, injection catheter 602 can be removed from the treatment site (FIG. 6E) and tubular structure 600 can remain in place for a time period deemed appropriate by a treating physician. Because the tubular structure 600 does not restrict the flow of fluids through the treated lumen, the bioactive materials can be held in place for a longer period of time than that allowed by previously available devices which blocked fluid flow.

The present invention also includes treatment kits comprising instructional information, a bioactive material delivery device and any appropriate form of injection catheter including injection tubes as described in relation to FIG. 4 and independent injection catheters as described in relation to FIGS. 5 and 6. Injection catheters used in accordance with the present invention can be coaxial catheters with, without limitation, two injection lumens or a dual lumen catheter or alternatively a three lumen catheter if a guide wire lumen is required. Injection catheters will have injection ports through bioactive materials may be delivered. One or more single lumen injection catheters can also be used in the place of multilumen injection catheters.

In certain embodiments, injection catheters that are used can include sensors to continuously (or intermittently) monitor conditions at the treatment site during bioactive material delivery. The sensors can be found anywhere along the injection catheter that, during bioactive material delivery, is near an injection port within a space. In injection catheter 602, a sensor 620 is found near injection port 606. Sensors that can be used in accordance with the present invention can include one or more of, without limitation, a pressure sensor, temperature sensor, pH sensor, blood sugar sensor, blood oxygen sensor, motion sensor, flow sensor, velocity sensor, acceleration sensor, force sensor, strain sensor, acoustic sensor, moisture sensor, osmolarity sensor, light sensor, turbidity sensor, radiation sensor, electromagnetic field sensor, chemical sensor, ionic sensor and/or enzymatic sensor. In one embodiment, the sensors of the present invention can employ wireless telemetry to deliver information from the treatment site to an instrument external to the body. In another embodiment, the sensors of the present invention can be constructed in accordance with the teachings of U.S. Pat. No. 5,704,352 to Tremblay and Buckles which is incorporated by reference. Alternatively, sensors as described in U.S. Pat. No. 6,632,196 to Houser, which is incorporated by reference can also be used. Other appropriate sensors include, without limitation, optical-fiber based transducers as manufactured by RJC Enterprises of Woodinville, Wash. and described in U.S. Pat. No. 6,052,613 to Takaki or as described in "Fiber-optic Transducer Aids Heart Monitoring," Engineering News, Jun. 7, 1999, both of which are incorporated herein by reference. A model FOP-M in-vivo pressure sensor, manufactured by FISO Technologies, of Quebec, Canada, also can be used in accordance with the present invention as well as other sensor constructions that are known to those of ordinary skill in the art.

As stated, in certain embodiments with or without the use of injection tubes or injection catheters, the biocompatible covering of the tubular structure can be coated with a bioactive material that will be released over time. Bioactive materials can be coated onto the surface of a biocompatible covering by, without limitation, spraying, rolling or dipping the tubular structure in a solution containing the bioactive material.

In certain embodiments when fluid is trapped in the bioactive material delivery space following expansion of the ring members, this fluid can be removed with the use of a vacuum. Bioactive materials can then delivered to the described space(s) through one or more injection tubes or catheters that run from outside of the patient's body to the treatment site or through release from the biocompatible covering. The proximal ends of the injection tubes or injection catheters will include appropriate features to allow for the controlled delivery of one or more bioactive materials to the treatment site. Once bioactive material delivery is complete, the retaining sheath, tensioning mechanism or other retraction mechanism can contract the tubular structure and the system can be removed from the treatment site. Other embodiments according to the present invention can be left at the treatment site for a longer period of time such as for, without limitation, long-term stenting or stent-grafting purposes.

Unless otherwise indicated, all numbers expressing quantities of ingredients, properties such as molecular weight, reaction conditions, and so forth are to be understood as being modified in all instances by the term "about." Accordingly, unless indicated to the contrary, the numerical parameters set forth are approximations that may vary depending upon the desired properties sought to be obtained. At the very least, each numerical parameter should at least be construed in light of the number of reported significant digits and by applying ordinary rounding techniques. Notwithstanding that the numerical ranges and parameters are approximations, the numerical values set forth in the specific examples are reported as precisely as possible. Any numerical value, however, inherently contains certain errors necessarily resulting from the standard deviation found in their respective testing measurements.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

While certain embodiments according to this invention are described herein, variations of those embodiments will become apparent to those of ordinary skill in the art upon reading the foregoing description.

Furthermore, numerous references have been made to patents and printed publications throughout this specification. Each of the above cited references and printed publications are herein individually incorporated by reference in their entirety.

What is claimed is:

1. A bioactive material delivery device for use at a treatment site in a lumen having an inner wall, the bioactive material delivery device comprising:
    a tubular structure comprising:
    two or more expandable ring members; and
    a biocompatible covering having a uniform natural diameter less than a diameter of the two or more expandable ring members, the biocompatible covering being connected to the two or more expandable ring members, the biocompatible covering having first portions in contact with the two or more expandable ring members and a second portion extending between an adjacent pair of the two or more expandable ring members, the first portions having a first expanded diameter and the second portion having a second expanded diameter, the second expanded diameter being less than the first expanded diameter;
    wherein, when said two or more expandable ring members are expanded, said two or more expandable ring members expand the second portion of said biocompatible covering not in direct contact with said two or more expandable ring members to the second expanded diameter less than the first expanded diameter of said expanded two or more expandable ring members, and expand the first portions from the natural diameter to the first expanded diameter, the first expanded diameter being selected to seal the first portions against the inner wall of said lumen and to prevent fluid flow between the first portions and the inner wall; and
    when said bioactive material delivery device is fully deployed at the treatment site within the lumen, an outer surface of the second portion of said biocompatible covering, the inner wall of said lumen, and the adjacent pair of the two or more expandable ring members define a bioactive material delivery space.

2. A bioactive material delivery device according to claim 1 wherein said tubular structure comprises ring members at positions selected from the group consisting of: at the ends of said tubular structure; at the ends of said tubular structure and spaced at regular intervals along the length of said tubular structure; and at the ends of said tubular structure and spaced at irregular intervals along the length of said tubular structure.

3. A bioactive material delivery device according to claim 1 wherein said tubular structure comprises undulating ring members at both ends of said tubular structure and wherein said undulating ring members are connected by an undulating helical wire along the length of said tubular device.

4. A bioactive material delivery device according to claim 1 wherein said tubular structure further comprises additional structural elements such that when said expandable ring members expand, said additional structural elements further define longitudinal or helical channels for bioactive material delivery.

5. A bioactive material delivery device according to claim 1 wherein said ring members are expanded by an expansion method selected from the group consisting of: self expansion; self expansion following retraction of a retaining sheath; self expansion following release from a tensioning mechanism; balloon expansion; and combinations thereof.

6. A bioactive material delivery device according to claim 1 wherein said biocompatible covering of said tubular structure comprises:
    an injection tube disposed within the biocompatible covering;
    at least one injection port connected to the second portion of the biocompatible covering, the injection port being in fluid communication between the injection tube and the bioactive material delivery space,
    wherein the injection tube is operable to deliver bioactive material from outside of a patient to the bioactive material delivery space.

7. A bioactive material delivery device according to claim 1 wherein said biocompatible covering is coated with a bioactive material that can be released into said spaces.

* * * * *